United States Patent
Chen et al.

(10) Patent No.: US 7,618,966 B2
(45) Date of Patent: Nov. 17, 2009

(54) ABNORMAL CANNABIDIOLS AS AGENTS FOR LOWERING INTRAOCULAR PRESSURE

(75) Inventors: June Chen, San Juan Capistrano, CA (US); Simon Pettit, Essex (GB); Hans Fliri, Essex (GB)

(73) Assignee: Allergan, Inc., Irvine, CA (US)

( * ) Notice: Subject to any disclaimer, the term of this patent is extended or adjusted under 35 U.S.C. 154(b) by 487 days.

(21) Appl. No.: 11/409,871

(22) Filed: Apr. 24, 2006

(65) Prior Publication Data

US 2007/0249602 A1 Oct. 25, 2007

(51) Int. Cl.
A01N 43/40 (2006.01)
C07D 211/08 (2006.01)
C07C 211/00 (2006.01)
C07C 39/17 (2006.01)

(52) U.S. Cl. .................... 514/235.2; 514/277; 514/646; 514/734; 514/741; 546/192; 564/305; 568/743; 568/811; 568/828

(58) Field of Classification Search ................ 514/277, 514/646, 734, 741
See application file for complete search history.

(56) References Cited

U.S. PATENT DOCUMENTS

| 2002/0137961 A1 | 9/2002 | Bradley et al. |
| 2002/0161041 A1 | 10/2002 | Browning et al. |
| 2003/0180234 A1 | 9/2003 | Love et al. |
| 2005/0282902 A1 | 12/2005 | Chen et al. |
| 2005/0282912 A1 | 12/2005 | Chen et al. |
| 2005/0282913 A1 | 12/2005 | Chen et al. |
| 2006/0247321 A1 | 11/2006 | Chen |
| 2007/0249581 A1 | 10/2007 | Chen et al. |
| 2007/0249596 A1 | 10/2007 | Chen et al. |
| 2007/0249731 A1 | 10/2007 | Chen et al. |

FOREIGN PATENT DOCUMENTS

| DE | 2839836 | 3/1979 |
| EP | 0119087 | 9/1984 |
| EP | 0492904 | 7/1992 |
| WO | WO 03/091189 | 11/2003 |
| WO | WO 2006/001982 | 1/2006 |
| WO | WO 2006/007227 | 1/2006 |
| WO | WO 2007/008548 | 1/2007 |

OTHER PUBLICATIONS

Peter C. Astles, et al, Selective Endothelin A Receptor Antagonists, 41 J. Med. Chem. 2732, 2734 (1998).*

Howlett et al, "International Union of Pharmacology. XXVII. Classification of Cannabinoid Receptors", Pharmacological Reviews, 54: 2002, pp. 161-202.
Cieplak et al, "Reversal of π-Facial Diastereoselection upon Electronegative Substitution of the Substrate and the Reagent", J. Am. Chem. Society, 1989, 111, pp. 8447-8462.
Micovic et al, "The synthesis of lactam analogues of fentanyl", J. Chem. Soc., Perkin Trans 1, 1996, pp. 2041-2050.
Wagner et al, "Mesenteric Vasodilation Mediated by Endothelial Anandamide Receptors", Hypertension. 33 [part II], 1999, pp. 429-434.
Jarai et al, Cannabinoid-induced mesenteric vasodilation through an endothelial site distinct from CB1 or CB2 receptors, PNAS, vol. 96, No. 24, 1999, pp. 14136-14141.
Pisanenko et al, "Anti Microbial Activity of Cyclo Alkenyl Phenos and 4-Alpha Arylcyclopentyl Phenols", Pharmaceutical Chemistry Journal, vol. 10, No. 10, 1997.
Adams et al, "Structure of Cannabidiol. IV. The position of the linkage between the two rings", J. Am. Chem. Soc., vol. 62, pp. 1774-1775, 1940.
Fujikawa et al, Antiseptics for foods. LXXIII. 3-Halo-4-hydroxy benzoic acid esters, 4-alkylresorcinol, 4-arylresorcinol, ..., Chemical Abstracts Database, XP00244503, 1972.
Arnoldi et al, "Analogues of Cannabinoids, Synthesis of N-Heterocyclic Derivatives of Olivetol", J. Chem., XP009087450, 1983.
Yorio et al, "New therapies for glaucoma: Are they all up to the task?", Expert Opinion on Therapeutic Patents 2004, vol. 14, No. 12, pp. 1743-1762, 2004.

* cited by examiner

*Primary Examiner*—Frederick Krass
*Assistant Examiner*—Sean Basquill
(74) *Attorney, Agent, or Firm*—Dean G. Stathakis; Joel B. German; Debra D. Condino

(57) ABSTRACT

The present invention provides a method of treating glaucoma or ocular hypertension which comprises applying to the eye of a person in need thereof an amount sufficient to treat glaucoma or ocular hypertension of a compound of formula I

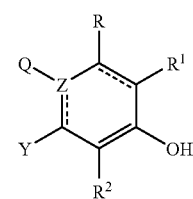

wherein Y, Q, Z, R, $R^1$ and $R^2$ are as defined in the specification.

The present invention further comprises pharmaceutical compositions, e.g. ophthalmic compositions, including said compound of formula I.

7 Claims, No Drawings

ABNORMAL CANNABIDIOLS AS AGENTS FOR LOWERING INTRAOCULAR PRESSURE

BACKGROUND OF THE INVENTION

1. Field of the Invention

The present invention relates to the use of Abnormal Cannabidiols to lower the intraocular pressure of mammals and thus are useful in treating glaucoma.

2. Background of the Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical α-adrenoreceptor antagonists have traditionally been the drugs of choice for treating glaucoma.

Certain Abnormal Cannabidiols are disclosed in Howlett et al, "International Union of Pharmacology. XXVII. Classification of Cannabinoid Receptors", Pharmacological Reviews 54:161-202, 2002.

Reference is made to Published U.S. Patent Application Nos. 2005/0282902, 2005/0282912 and 2005/0282913 to Chen et al which were published on Dec. 22, 2005 and are herein incorporated by reference thereto. (June Chen is a co-inventor of each of said published patent applications and the present patent application.)

SUMMARY OF THE INVENTION

We have found that Abnormal Cannabidiols are potent ocular hypotensive agents. We have further found that Abnormal Cannabidiols and homologues and derivatives thereof, are especially useful in the treatment of glaucoma and surprisingly, cause no or significantly lower ocular surface hyperemia than the other compounds that are useful in lowering intraocular pressure, e.g. $PGF_{2\alpha}$ and lower alkyl esters thereof.

The present invention relates to methods of treating ocular hypertension and glaucoma which comprises administering an effective amount of a compound represented by the formula I

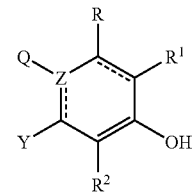

Y is selected from the group consisting of O and OH;
Z is N or C;
Q is selected from the group consisting of

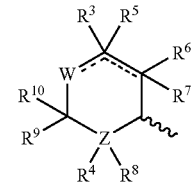

W is a direct bond or $C(R^{11})(R^{12})$;
a dotted line represents the presence or absence of a double bond;
R is selected from the group consisting of H, halogen, e.g. bromo or chloro; and $C_{1-5}$ alkyl;
$R^1$ is selected from the group consisting of H and halogen, e.g. bromo or chloro;
$R^2$ is independently selected from the group consisting of H, $C_{1-5}$ alkyl, halogen, $XC_{1-5}$ alkyl, $C_{1-5}$ alkyl$OR^{13}$, $C_{1-5}$ alkyl$N(R^{13})_2$, $N(R^{13})_2$, $XC_{1-5}$ alkyl$N(R^{13})_2$ and $XC_{1-5}$ alkyl$OR^{13}$;
X is O or $S(O)_n$;
n is 0 or an integer of from 1 to 2;
$R^3$ is selected from the group consisting of H, hydroxyl, $C_{1-5}$ alkyl, $C_{1-5}$ alkyl$OR^{13}$ and $C_{1-5}$ alkyl$N(R^{13})_2$;
$R^4$ is selected from the group consisting of H, $C_{2-5}$ alkenyl, e.g. isopropenyl, $C_{1-5}$ alkyl, $C_{1-5}$ alkyl$OR^{13}$ and $C_{1-5}$ alkyl$N(R^{13})_2$;
$R^5$, $R^6$, $R^7$, $R^8$, $R^9$, $R^{10}$, $R^{11}$, $R^{12}$ are independently selected from the group consisting of H, $C_{1-5}$ alkyl, $C_{1-5}$ alkyl$OR^{13}$ and $OR^{13}$; and
$R^{13}$ is selected from the group consisting of H, $C_{1-5}$ alkyl and $C_{3-8}$ cyclic alkyl, or two $R^{13}$ groups, together with N or O, may form a cyclic ring such as a piperidine or morpholine ring; and provided that any of said alkyl groups may be substituted with a hetero atom containing radical, wherein said heteroatom is selected from the group consisting of halogen, e.g. fluoro, chloro or bromo, oxygen, nitrogen and sulfur, e.g. hydroxyl, amino, nitro, mercapto, etc.;
$R^8$ and $R^{12}$ may, together, form a cyclic ring;
and $R^3$ and $R^5$ may, together, represent O, and
when Q is menthadiene, $R^1$ and $R^2$ are H and Y is hydroxyl, R may not be H or alkyl.

In a further aspect, the present invention relates to pharmaceutical compositions comprising a therapeutically effective amount of a compound of formulae (I), in admixture with an non-toxic, pharmaceutically acceptable liquid vehicle. Such pharmaceutical compositions may be ophthalmic solutions which are useful in treating ocular hypertension and/or glaucoma. Finally, the present invention provides certain novel compounds which are useful in treating ocular hypertension and/or glaucoma.

DETAILED DESCRIPTION OF THE INVENTION

The present invention relates to the use of Abnormal Cannabidiols as ocular hypotensives. These therapeutic agents are represented by compounds having the formula I, above.

In one embodiment of the invention, the compound is selected from the group consisting of abnormal Cannabidiols and analogues thereof represented by formula II.

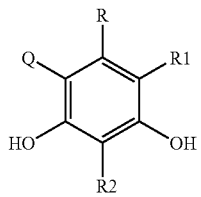

II wherein Q is selected from the group consisting of

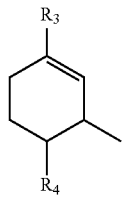 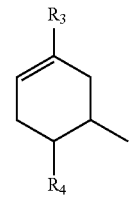 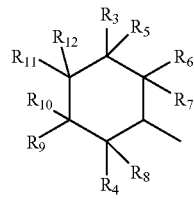

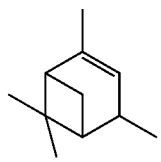 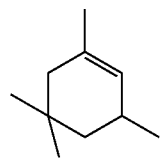 and

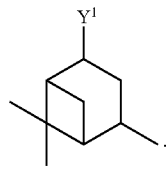

wherein R, $R^1$, $R^2$, $R^3$, $R^4$, $R^5$, $R^6$, $R^7$, $R^8$, $R^9$, $R^{10}$, $R^{11}$, $R^{12}$ and Q are as defined above and $Y^1$ is $R^3$ and $R^5$, or O, or OH.

A particularly preferred group represented by Q is menthadiene or

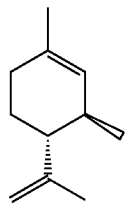

In this class of compounds, preferably, R is selected from the group consisting of hydrogen, methyl, bromo and chloro and $R^1$ is selected from the group consisting of hydrogen, methyl and chloro.

Compounds of this type may be prepared by condensation of a cyclic alkene or cyclic alcohol with a suitably substituted benzene-1,3-diol. The reaction is catalysed by an acid such as oxalic acid dihydrate or p-toluenesulphonic acid. The reaction is carried out in a solvent or mixture of solvents such as toluene, diethyl ether or dichloromethane. A mixture of the two isomers is obtained and the desired product is separated by chromatography. The reaction scheme is illustrated below.

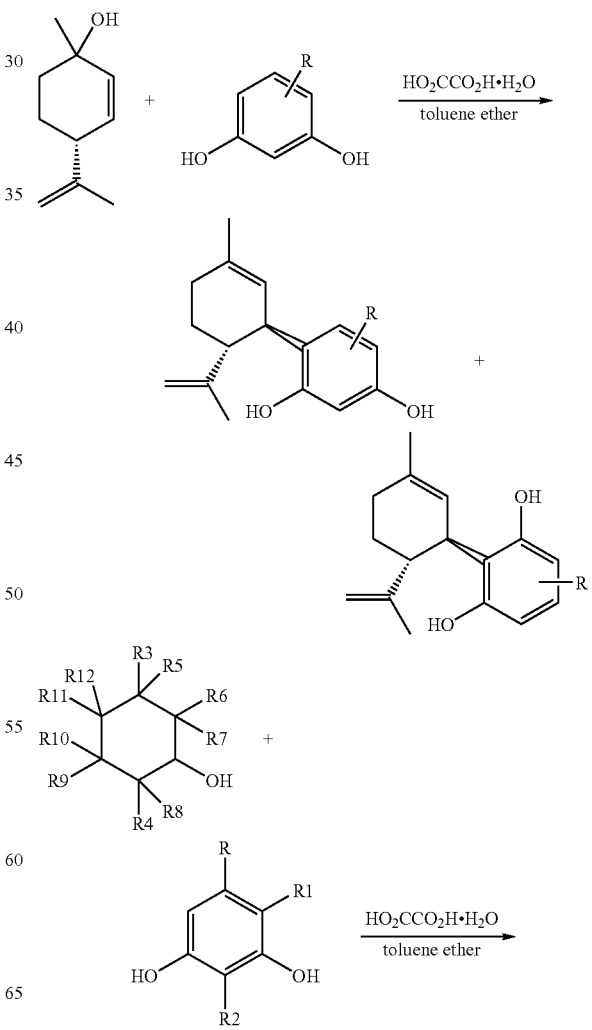

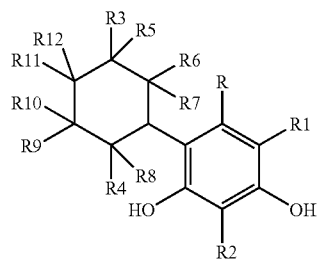

The synthesis of the starting materials is well known.

The mechanism of the reaction is the result of the formation of a carbocation by elimination of OH or a starting material containing a functional group such as acetate which can also be eliminated to give the carbocation can be used.

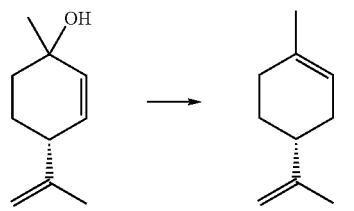

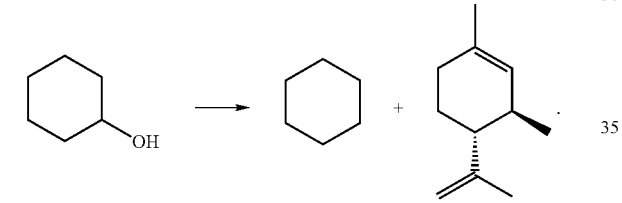

In another embodiment of the invention the compound is tetrahydropyridine represented by formula III.

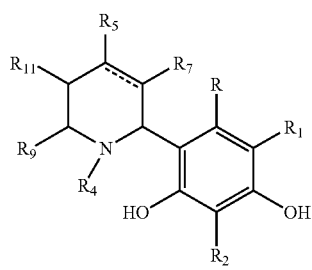

III

These tetrahydropyridine compounds may be synthesized according to the following reaction scheme wherein Me is methyl, Bu is butyl and iPr is isopropyl.

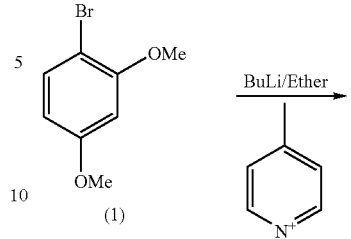

(1)

(2) $R^4$ = Me
(3) $R^4$ = $^i$Pr

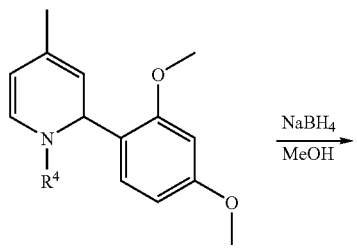

(4) $R^4$ = Me
(5) $R^4$ = $^i$Pr

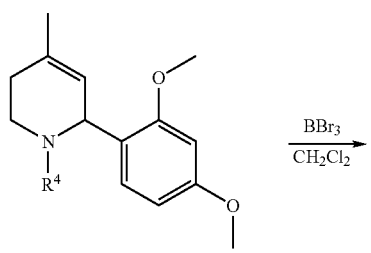

(6) $R^4$ = Me
(7) $R^4$ = $^i$Pr

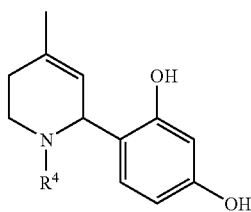

(8) $R^4$ = Me
(9) $R^4$ = $^i$Pr

In a further embodiment of the invention, the group Q may be substituted by a carbonyl or hydroxy group. These compounds may be prepared by the following schemes

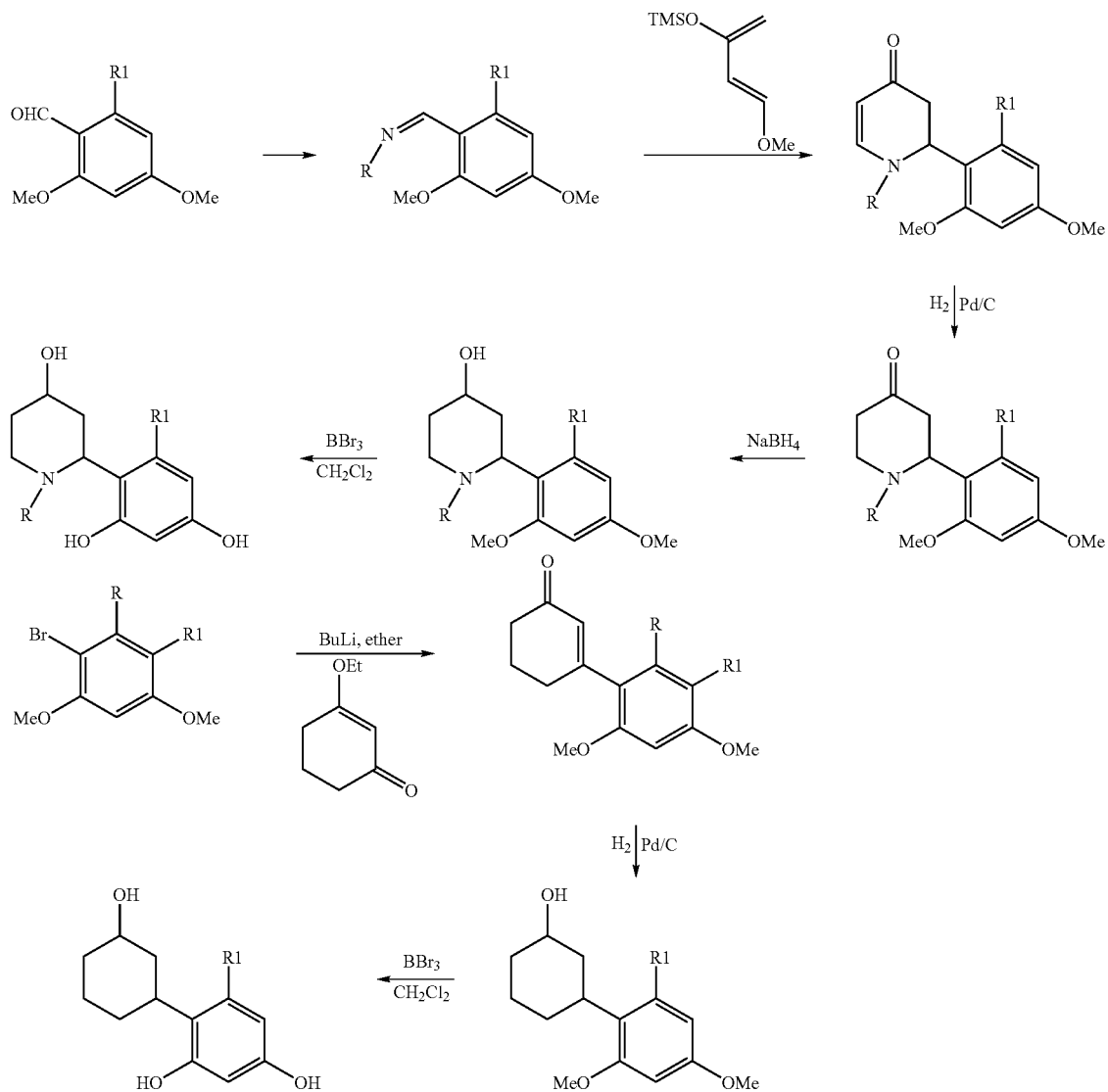
As described in JACS, 1989, 8447-8462
In a further embodiment of the invention, the compound is a piperidinedione represented by the formula IV
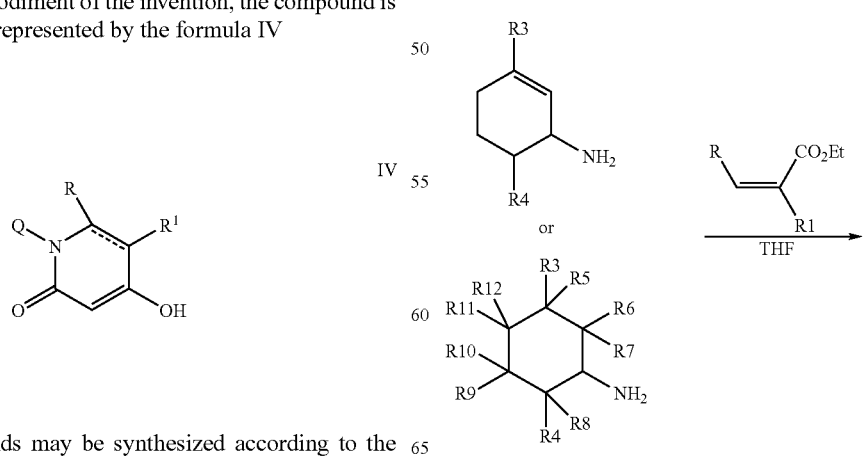
These compounds may be synthesized according to the following reaction scheme wherein Et is ethyl, THF is tetrahydrofuran and DCM is dichloromethane.

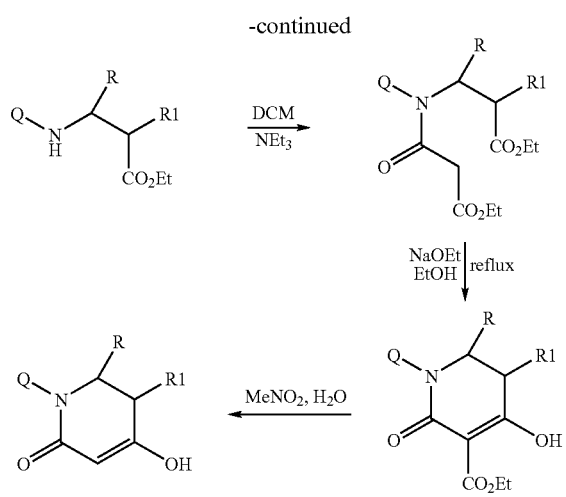

An alternative base and solvent for the cyclisation is potassium carbonate, 18-crown-6 in toluene at reflux or sodium hydride in cyclohexane at reflux, as described by I. V. Micovic et al, J. Chem. Soc. Perkin I, 1996, 2041-2050. The decarboxylation can also be carried out with 10% aqueous oxalic acid.

In all of the above formulae, as well as in those provided hereinafter, the straight lines represent bonds. Where there is no symbol for the atoms between the bonds, the appropriate carbon-containing radical is to be inferred.

Pharmaceutical compositions may be prepared by combining a therapeutically effective amount of at least one compound according to the present invention, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five unit doses, where a typical unit dose is from one to about 8 drops, preferably one to about 3 drops. The volume of one drop usually is about 20-35 μl.

The compounds disclosed herein for use in the method of this invention, i.e. the treatment of glaucoma or elevated intraocular pressure, may also be used in combination with other drugs useful for the treatment of glaucoma or elevated intraocular pressure.

For the treatment of glaucoma or elevated intraocular pressure, combination treatment with the following classes of drugs are contemplated:

β-Blockers (or β-adrenergic antagonists) including carteolol, levobunolol, metipranolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and α$_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarpine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, isopropyl unoprostone, latanoprost and the like.

The invention is further illustrated by the following non-limiting Examples.

EXAMPLE 1

Intraocular Pressure

Intraocular pressure was measured by applanation pneumatonometry in conscious animals. The test compound was administered topically to one eye while vehicle was given to the fellow eye in a masked fashion. Laser-induced unilaterally ocular hypertensive Cynomolgus monkeys (females) were dosed once and the IOP was measured over the course of 24 hours.

The results are shown in the Table, below wherein the stars indicating the potency of the compound. That is, one star indicates no potency, three stars indicates a very potent compound.

| Example No. | Efficacy |
| --- | --- |
| Vehicle | * |
| 5 | *** |
| 16 (c) Tetrahydropyridine derivative | ** |
| 20 Piperidinedione derivative | *** |
| 9 (b) Cyclohexane derivative | *** |

EXAMPLE 2

Determination of Abnormal Cannabidiol Activity

Abnormal Cannabidiol receptor activity may be measured in accordance with the procedure disclosed in (Wagner J A et al., *Hypertension* 33 [part II], 429 (1999); Járai Z et al., *PNAS* 96, 14136 (1999), which is hereby incorporated by reference in its entirety.

When measured according to this assay all of the compounds of the Examples, below, are found to be active.

Experimental Details for Synthesis of Abnormal Cannabidiols

General Route

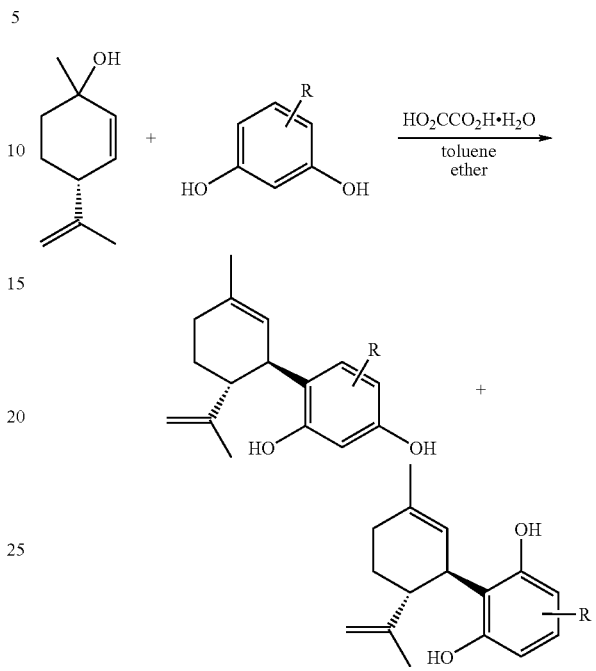

EXAMPLE 3

Synthesis of 4-(6-Isopropenyl-3-methylcyclohex-2-enyl)-5-methylbenzene-1,3-diol (4R)-1-Methyl-4-isopropenylcyclohex-2-ene-1-ol (300 mg, 2 mmoles) was dissolved in toluene (20 ml) and 5-methylresorcinol (248 mg, 2 mmoles) was added in diethyl ether (5 ml). Oxalic acid dihydrate (252 mg, 2 mmoles) was added and the reaction mixture heated with stirring at 80° for 5 hours. The reaction mixture was allowed to cool and diluted with diethyl ether (30 ml). The ether solution washed twice with aqueous sodium bicarbonate and dried over anhydrous magnesium sulphate. The solvents were evaporated under reduced pressure to give the crude product as a brown oil (800 mg). The product was purified using a silica column eluted with ethyl acetate:isohexane 1:9 going to ethyl acetate:isohexane 2:8.

The product was isolated as a yellow gum (106 mg)

$^1$H NMR (300 MHz, CDCl$_3$) 6.2 (M, 2H), 6.1 (S, 1H), 5.55 (M, 1H), 4.7 (M, 1H), 4.55 (S, 1H), 4.5 (M, 1H), 3.55 (M, 1H), 2.5 (M, 1H), 2.2 (M, 2H), 2.15 (S, 3H), 1.85 (M, 2H), 1.8 (S, 3H), 1.6 (S, 3H)

The reaction product is recovered using a silica column eluted with ethyl acetate:isohexane 1:9 going to ethyl acetate:isohexane 2:8.

The product was isolated as a yellow gum (106 mg)

$^1$H NMR (300 MHz, CDCl$_3$) 6.2 (M, 2H), 6.1 (S, 1H), 5.55 (M, 1H), 4.7 (M, 1H), 4.55 (S, 1H), 4.5 (M, 1H), 3.55 (M, 1H), 2.5 (M, 1H), 2.2 (M, 2H), 2.15 (S, 3H), 1.85 (M, 2H), 1.8 (S, 3H), 1.6 (S, 3H)

Also prepared in a similar manner were:

EXAMPLE 4

4-(6-Isopropenyl-3-methylcyclohex-2-enyl)benzene-1,3-diol $^1$H NMR (300 MHz, CDCl$_3$) 6.8 (D, 1H J=8 Hz), 6.35 (M, 1H), 6.3 (M, 1H), 5.6 (S, 1H), 5.5 (S, 1H), 4.7 (M, 1H), 3.35 (M, 1H), 2.3 (M, 1H), 2.1 (M, 2H), 1.8 (M, 2H), 1.85 (S, 3H), 1.6 (S, 3H)

EXAMPLE 5

5-Chloro-4-(6-Isopropenyl-3-methylcyclohex-2-enyl)benzene-1,3-diol $^1$H NMR (300 MHz, CDCl$_3$) 6.4 (M, 1H), 6.3 (M, 1H), 6.25 (S, 1H), 5.6 (M, 1H), 4.7 (brS, 1H), 4.65 (M, 1H), 4.4 (M, 1H), 4.0 (M, 1H), 2.5 (M, 1H), 2.25 (M, 1H), 2.15 (M, 1H), 1.85 (M, 2H), 1.8 (S, 3H), 1.6 (S, 3H)

EXAMPLE 6

4-(6-Isopropenyl-3-methylcyclohex-2-enyl)-5-methoxybenzene-1,3-diol $^1$H NMR (300 MHz, CDCl$_3$) 6.15 (brS, 1H), 6.0 (M, 2H), 5.6 (M, 1H), 4.65 (brS, 1H), 4.5 (M, 1H), 4.35 (M, 1H), 3.95 (M, 1H), 3.7 (S, 3H), 2.4 (M, 1H), 2.25 (1H, M), 2.1 (M, 1H), 1.8 (M, 2H), 1.8 (S, 3H), 1.65 (S, 3H)

EXAMPLE 7

2-(6-Isopropenyl-3-methylcyclohex-2-enyl)-5-methoxybenzene-1,3-diol $^1$H NMR (300 MHz, CDCl$_3$) 6.0 (brS, 2H), 5.55 (M, 1H), 4.7 (M, 1H), 4.6 (M, 1H), 3.8 (M, 1H), 3.75 (S, 3H), 2.4 (M, 1H), 2.2 (M, 1H), 2.1 (M, 1H), 1.8 (S, 3H), 1.8 (M, 2H)

EXAMPLE 8(a)

Synthesis of 6-Chloro-4-(6-Isopropenyl-3-methylcyclohex-2-enyl)benzene-1,3-diol 4-Chlororesorcinol (350 mg, 2.4 mmoles) was dissolved in toluene (30 ml) and diethyl ether (20 ml) and p-toluenesulphonic acid (91 mg, 0.48 mmoles) was added.

(4R)-1-Methyl-4-isopropenylcyclohex-2-ene-1-ol (500 mg, 3 mmoles) in toluene (10 ml) was added and the reaction mixture was stirred at room temperature for 6 hours. Diluted with diethyl ether (30 ml) and washed twice with aqueous sodium bicarbonate. Dried over anhydrous magnesium sulphate and the solvent was evaporated under reduced pressure to give a yellow gum (800 mg). Purified using a silica column eluted with ethyl acetate:isohexane 9:1 going to ethyl acetate:isohexane 8:2. The product was isolated as a yellow gum (95 mg)

$^1$H NMR (300 MHz, CDCl$_3$) 6.9 (S, 1H), 6.5 (S, 1H), 5.5 (S, 1H), 5.45 (M, 1H), 5.35 (S, 1H), 4.7 (M, 1H), 4.6 (M, 1H), 3.35 (M, 1H), 2.2 (M, 3H), 1.8 (M, 3H), 1.75 (M, 2H), 1.6 (S, 3H)

Examples 8(b) and 8(c) are made by the same method as example 8(a) using cis-verbenol instead of (4R)-1-Methyl-4-isoprenylcyclohex-2-ene-1-ol.

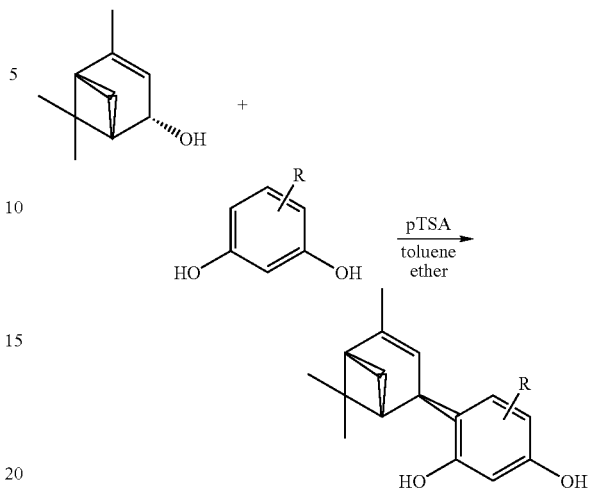

EXAMPLE 8(b)

5-Methyl-4-(4,6,6-trimethyl-bicyclo[3.1.1]hept-3-en-2-yl)benzene-1,3-diol $^1$H NMR (300 MHz, CDCl$_3$) 7.35 (brs, 1H), 6.25 (m, 1H), 6.2 (m, 1H), 5.7 (m, 1H), 4.75 (brs, 1H), 3.7 (m, 1H), 2.35 (m, 1H), 2.2 (s, 3H), 2.15 (m, 1H), 1.9 (S, 3H), 1.6 (d, 1H), 1.35 (s, 3H), 1.0 (s, 3H)

EXAMPLE 8(c)

5-Chloro-4-(4,6,6-trimethyl-bicyclo[3.1.1]hept-3-en-2-yl)benzene-1,3-diol $^1$H NMR (300 MHz, CDCl$_3$) 7.55 (s, 1H), 6.5 (m, 1H), 6.25 (m, 1H), 5.7 (m, 1H), 5.45 (s, 1H), 4.0 (m, 1H), 2.3 (m, 1H), 2.2 (m, 1H), 1.9 (S, 3H), 1.5 (d, 1H), 1.35 (s, 3H), 1.0 (s, 3H)

EXAMPLE 9(a)

Synthesis of 4-Cyclohexylbenzene-1,3-diol

This compound was prepared as described in JACS, 1953, 2341.

Resorcinol (2.2 g, 0.02 moles) was mixed with cyclohexanol (1 g, 0.01 moles) and zinc (II) chloride (0.48 g, 0.0035 moles) and the reaction mixture heated to 150° with stirring. After heating 2 hours, the reaction mixture was allowed to cool and then dissolved in ethyl acetate. Washed with water and dried over anhydrous magnesium sulphate. The solvent was evaporated to give a brown oil (3.0 g). Excess resorcinol was evaporated by heating in a Kugelrohr oven under reduced pressure (200°, 2 mmHg). Purified using a silica column eluted with ethyl acetate: isohexane 2:8 to give the product as a yellow oil (0.5 g). Trituration with isohexane gave the product as a white solid (0.2 g).

EXAMPLE 9(b)

5-Chloro-4-cyclohexylbenzene-1,3-diol

Example 9(b) was made by the same method as Example 9(a).

¹H NMR (300 MHz, CDCl₃) 7.0 (D, 1H J=8 Hz), 6.4 (M, 1H), 6.3 (M, 1H), 4.7 (S, 1H), 4.55 (S, 1H), 2.7 (M, 1H), 1.8 (M, 5H), 1.4 (M, 5H)

EXAMPLE 10

Synthesis of 4R-Isopropenyl-1-methylcyclohex-2-enol

The synthesis of 4R-Isopropenyl-1-methylcyclohex-2-enol was carried out as described in WO2004096740.

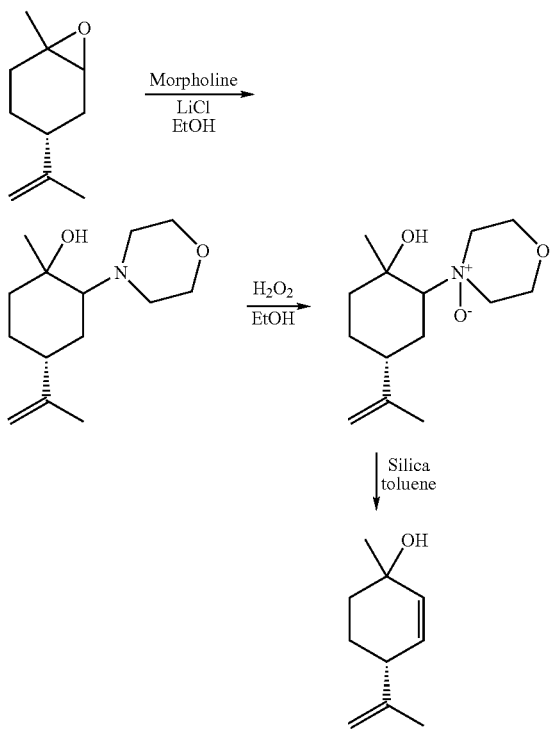

EXAMPLE 11

4-Isopropenyl-1-methyl-2-morpholin-4-yl-cyclohexanol (+)-Limonene oxide (13.2 g, 0.087 moles) was dissolved in ethanol (40 ml) and lithium chloride (5.9 g, 0.14 moles) was added with stirring. Morpholine (11.4 g, 0.13 moles) was added and the reaction mixture was heated at 60° for 48 hours. The solvent was evaporated under reduced pressure and the residue taken up in dichloromethane. Washed with water. Extracted into 2M hydrochloric acid and washed with dichloromethane. Basified to pH 10 by addition of 2M sodium hydroxide. Extracted with diethyl ether and washed with water. Dried over anhydrous magnesium sulphate and evaporated the solvent under reduced pressure to give the product as a yellow oil (10.3 g)

¹H NMR (300 MHz, CDCl₃) 4.95 (M, 1H), 4.85 (M, 1H), 3.7 (M, 4H), 2.75 (M, 2H), 2.5 (M, 4H), 2.1 (M, 1H), 1.95 (M, 1H), 1.75 (S, 3H), 1.6 (M, 4H), 1.2 (S, 3H)

EXAMPLE 12

4-Isopropenyl-1-methyl-2-(4-oxy-morpholin-4-yl)-cyclohexanol

4-Isopropenyl-1-methyl-2-morpholin-4-yl-cyclohexanol (17.7 g, 0.074 moles) was dissolved in ethanol (100 ml) and 35% hydrogen peroxide (37 ml, 0.325 moles) was added. Heated with stirring at 50° for 6 hours. 5% palladium on carbon (100 mg) was added in order to decompose the excess peroxide. Stirred at room temperature for 3 hours. (Peroxide test papers gave a negative result.)

Filtered through a pad of HiFlo to remove the palladium on carbon and the solvent was evaporated under reduced pressure to give the product as a yellow oil (22.2 g).

¹H NMR (300 MHz, CDCl₃) 5.5 (M, 1H), 4.85 (M, 1H), 4.5 (M, 2H), 3.7 (M, 4H), 3.4 (M, 3H), 2.95 (M, 1H), 2.65 (M, 1H), 2.25 (M, 1H), 2.0 (M, 1H), 1.85 (M, 1H), 1.75 (M, 1H), 1.75 (S, 3H), 1.55 (M, 1H), 1.55 S, 3H)

EXAMPLE 13

4R-Isopropenyl-1-methylcyclohex-2-enol

4-Isopropenyl-1-methyl-2-morpholin-4-yl-cyclohexanol (4.6 g, 0.018 moles) was dissolved in toluene (80 ml) and silica (1.1 g) was added. The reaction mixture was heated to reflux with stirring. Water generated in the reaction was removed using Dean and Stark apparatus. After refluxing overnight, the silica was removed by filtration and the filtrate evaporated under reduced pressure to give a brown oil (4.0 g). Dissolved in dichloromethane and washed with 2M hydrochloric acid. Washed with water and dried over anhydrous magnesium sulphate. The solvent was removed by evaporation under reduced pressure to give the product as a brown oil (1.3 g).

¹H NMR (300 MHz, CDCl₃) 5.7 (M, 2H), 4.8 (M, 2H), 2.7 (M, 1H), 1.8 (M, 2H), 1.75 (S, 3H), 1.65 (M, 2H), 1.3 (S, 3H)

Experimental Details for Synthesis of Tetrahydropyridines

Scheme 1

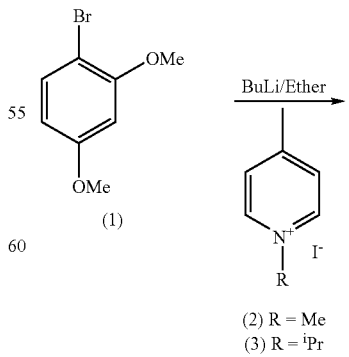

(2) R = Me
(3) R = ⁱPr

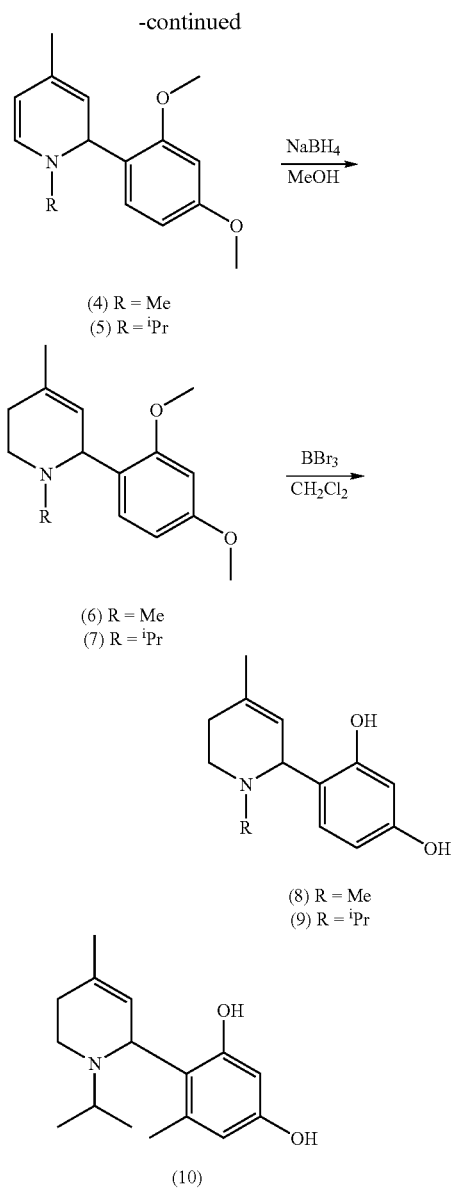

(4) R = Me
(5) R = ᶦPr (6) R = Me
(7) R = ᶦPr (8) R = Me
(9) R = ᶦPr (10)

EXAMPLE 14

Preparation of 2-(2,4-Dimethoxyphenyl)-1,4-dimethyl-1,2-dihydropyridine (4)

To a stirred solution of 2,4-dimethoxybromobenzene (1) (0.5 g, 2.3 mmol) in diethyl ether (10 ml) cooled at −78° C. under nitrogen was added a solution of n-butyl lithium (1.0 ml, 2.5 mmol of 2.5M solution in hexane) drop wise. The mixture was stirred at −78° C. for 2 hours and then 1,4-dimethylpyridinium iodide (2) (0.54 g, 2.5 mmol) was added as a solid. The resultant mixture was allowed to warm to room temperature and stirred at room temperature for 18 hours. The mixture was diluted with water (20 ml) and extracted with diethyl ether (2×15 ml). The combined organic extracts were dried over anhydrous magnesium sulphate, filtered and evaporated to yield 2-(2,4-dimethoxyphenyl)-1,4-dimethyl-1,2-dihydropyridine (4) (0.5 g, 93%) as a brown oil, $^1$H NMR CDCl$_3$ ??1.7 (s, 3H), 2.7 (s, 3H), 3.8 (s, 6H), 4.45 (dd, 1H, J=2.7) 4.85 (m, 1H), 5.4 (d, 1H, J=4), 6.05 (d, 1H, J=7), 6.45 (d, 1H, J=3), 6.55 (m, 1H), 7.5 (d, 1H, J=9).

By proceeding in a similar manner starting from 2,4-dimethoxybromobenzene (1) and 1-isopropyl-4-methylpyridinium iodide (3), 2-(2,4-dimethoxyphenyl)-1-isopropyl-4-methyl-1,2-dihydropyidine (5) was prepared, $^1$H NMR CDCl$_3$? (d, 6H J=7), 1.7 (s, 3H), 3.15 (m, 1H), 3.7 (s, 6H), 4.5 (d, 1H J=8), 4.8 (m, 1H), 5.5 (5, 1H J=5), 6.3 (d, 1H J=7), 6.45 (d, 1H J=2), 6.55 (m, 1H), 7.55 (d, 1H J=8).

EXAMPLE 15

Preparation of 6-(2,4-Dimethoxyphenyl)-1,4-dimethyl-1,2,3,6-tetrahydro-pyridine (6)

To a stirred solution of 2-(2,4-dimethoxyphenyl)-1,4-dimethyl-1,2-dihydropyridine(4) (0.48 g, 2.06 mmol) in methanol (5 ml) at room temperature was added sodium borohydride (98 mg, 2.51 mmol), gas evolution commenced immediately, the resulting mixture was stirred for 3 hours. At this time the solvent was evaporated and the residue suspended in water (5 ml) and extracted with ethyl acetate (2×10 ml). The organic extract was then extracted with 2M hydrochloric acid (2×15 ml). The aqueous layer was basified with 2M sodium hydroxide and extracted with ethyl acetate (2×20 ml), the organic extract was dried over anhydrous magnesium sulphate, filtered and evaporated to yield 6-(2,4-dimethoxyphenyl)-1,4-dimethyl-1,2,3,6-tetrahydropyridine (6) (350 mg, 73%) as a yellow oil, $^1$H NMR CDCl$_3$ δ?1.55 (s, 3H), 1.9 (m, 1H), 2.2 (s, 3H), 2.5 (m, 2H), 2.95 (m, 1H), 3.8 (s, 6H), 4.1 (m, 1H), 5.2 (m, 1H), 6.5 (m, 2H), 7.3 (d, 1H J=4).

By proceeding in a similar manner starting from 2-(2,4-dimethoxyphenyl)-1-isopropyl-4-methyl-1,2-dihydropyidine (5), 6-(2,4-dimethoxyphenyl)-1-isopropyl-4-methyl-1,2,3,6-tetrahydropyridine (7) was prepared, $^1$H NMR CDCl$_3$ δ 0.95 (d, 3H J=6), 1.05 (d, 3H J=6), 1.7 (s, 3H), 1.9 (m, 1H), 2.5 (m, 1H), 2.85 (m, 1H), 3.0 (m, 1H), 3.8 (s, 6H), 4.6 (s, 1H), 5.2 (s, 1H), 6.45 (d, 1H J=3), 6.5 (dd, 1H J=3.8), 7.4 (d, 1H J=8).

EXAMPLE 16(a)

Preparation 4-(1,4-Dimethyl-1,2,5,6-tetrahydropyridin-2-yl)-benzene-1,3-diol (8)

To a stirred solution of 6-(2,4-dimethoxyphenyl)-1,4-dimethyl-1,2,3,6-tetrahydro-pyridine (6) (300 mg, 1.27 mmol) in dichloromethane (20 ml) cooled at 0° C. under nitrogen was added boron tribromide (3.1 ml, 3.18 mmol of 1.0M solution in dichloromethane), the resultant dark solution was allowed to warm to room temperature and stirred for 1 hour. The solution was poured onto ice and basified with sodium bicarbonate. The layers were separated and the aqueous layer was extracted with dichloromethane (20 ml), the combined organic layers were dried over anhydrous magnesium sulphate, filtered and evaporated to a gum (200 mg). The material was purified on a 10 g silica cartridge eluting with methanol/dichloromethane/ammonia (7:92:1) to yield 4-(1,4-dimethyl-1,2,5,6-tetrahydropyridin-2-yl)-benzene-1,3-diol (8) (93 mg, 35%) as a gum, $^1$H NMR D6-acetone ??1.67 (s, 3H), 1.97 (m, 1H), 2.3 (s, 3H), 2.42 (m, 1H), 2.74 (m, 1H), 3.08 (m, 1H), 3.74 (s, 1H), 5.15 (s, 1H), 6.2 (d, 1H J=2), 6.27 (dd, 1H J=2.8), 6.82 (d, 1H J=8), 9.4 (bs, 2H).

EXAMPLE 16(b)

By proceeding in a similar manner starting from 6-(2,4-dimethoxyphenyl)-1-isopropyl-4-methyl-1,2,3,6-tetrahydropyridine (7), 4-(1-isopropyl-4-methyl-1,2,5,6-tetra-hydropyridin-2-yl)-benzene-1,3-diol (9) was prepared, NMR D6-acetone δ 0.81 (d, 3H J=7), 0.98 (d, 3H J=7), 1.52 (s, 3H), 1.84 (m, 1H), 2.15 (m, 1H), 2.29 (m, 1H), 2.94 (m, 2H), 4.09 (s, 1H), 4.97 (s, 1H), 6.05 (d, 1H J=3), 6.11 (dd, J=3.8), 6.68 (d, J=8), 9.6 (bs, 2H).

EXAMPLE 16(c)

By proceeding in a similar manner 4-(1-isopropyl-4-methyl-1,2,5,6-tetra-hydropyridin-2-yl)-5-methylbenzene-1,3-diol (10) was prepared, NMR CDCl$_3$δ 1.0 (d, 3H), 1.15 (d, 3H), 1.7 (s, 3H), 1.95 (m, 1H), 2.2 (s, 3H), 2.4 (m, 2H), 3.1 (m, 2H), 4.55 (m, 1H), 5.15 (m, 1H), 6.2 (m, 2H)

EXAMPLE 17

Preparation of 1-Isopropyl-4-methylpyridinium iodide (3)

To a stirred solution of 4-picoline (2.5 g, 26.8 mmol) in acetonitrile (50 ml) was added isopropyl iodide (9.1 g, 53.6 mmol) drop wise, the resultant mixture was heated at 90° C. for 24 hours. After cooling the solvent was evaporated to give a red solid which on trituration with ethyl acetate yielded 1-isopropyl-4-methylpyridinium iodide (6.01 g, 85%) as a cream solid, $^1$H NMR D6-DMSO δ?1.6 (d, 6H, J=7), 2.6 (s, 3H), 4.95 (m, 1H), 8.0 (d, 2H J=6), 9.05 (d, 2H J=6).

Experimental Details for Preparation of Piperidine-2,4-diones

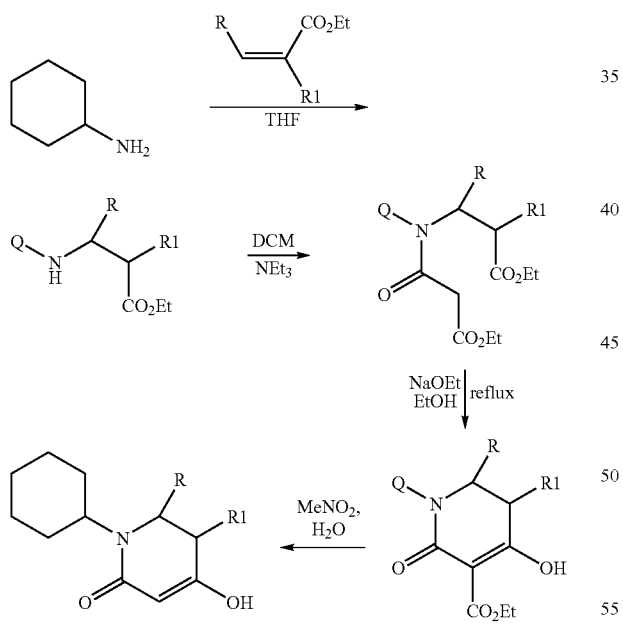

These compounds may also be prepared as described in J. Chem. Soc. Perkin I 1996, 2041-2050.

EXAMPLE 18

Preparation of Ethyl 1-cyclohexyl-piperidine-2,4-dione-3-carboxylate

N-Cyclohexyl-N-(2-ethoxycarbonyl-ethyl)-malonamic acid ethyl ester (5.40 g, 17.2 mmol) was heated with sodium ethoxide (2.34 g, 3.44 mmol) in refluxing ethanol (100 ml) for 3 hours. The cooled solution was concentrated, water (100 ml) was added and the solution washed with ether then isohexane. It was acidified with c. sulphuric acid to pH 2. The oily precipitate was extracted into dichloromethane, wahed with brine, dried (MgSO$_4$) and concentrated to a yellow oil weighing 3.6 g (67%).

EXAMPLE 19

Preparation of 1-Cyclohexyl-piperidine-2,4-dione

1-Cyclohexyl-2,4-dioxo-piperidine-3-carboxylic acid ethyl ester (3.1 g, 11.6 mmol) was heated with water (0.25 ml, 13.9 mmol) in nitromethane (30 ml) at 95° C. for 1 hour. The solution was concentrated to give an off-white solid weighing 2.3 g (93%). A sample was recrystallised from toluene.
$^1$H NMR (CDCl$_3$, ppm) δ 1.05-1.90 (m, 10H), 2.56 (t, 2H), 3.38 (s, 2H), 3.55 (t, 2H), 4.50 (m, 1H).

Also prepared in a similar manner was

EXAMPLE 20

Preparation of 1-Cyclohexyl-6-methylpiperidine-2,4-dione $^1$H NMR (CDCl$_3$, ppm) δ 1.05-1.95 (m, 13H), 2.56 (m, 2H), 3.35 (m, 2H), 3.96 (m, 1H), 4.50 (m, 1H).

It is apparent to one of ordinary skill in the art that different pharmaceutical compositions may be prepared and used with substantially the same results. That is, other Abnormal Cannabidiols will effectively lower intraocular pressure in animals and are within the scope of the present invention. Also, the novel compounds of the present invention may be used in a method of providing neuroprotection to the eye of a mammal in a similar manner to the abnormal Cannabidiols of Published U.S. Patent Application 2005/0282912.

The invention claimed is:
1. A compound of formula III

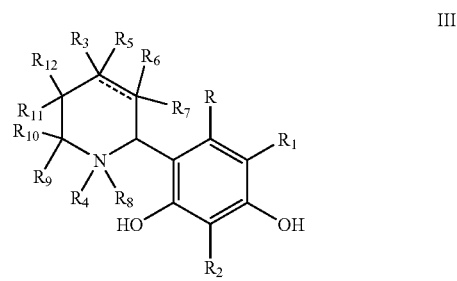

wherein a dotted line represents the presence or absence of a double bond;

R is selected from the group consisting of H, halogen and $C_{1-5}$ alkyl;

$R_1$ is selected from the group consisting of H and halogen;

$R_2$ is independently selected from the group consisting of H, $C_{1-5}$ alkyl, halogen, $XC_{1-5}$ alkyl, $C_{1-5}$ alkylOR$_{13}$, $C_{1-5}$ alkylN(R$_{13}$)$_2$, N(R$_{13}$)$_2$, $XC_{1-5}$ alkylN(R$_{13}$)$_2$ and $XC_{1-5}$ alkylO—R$_{13}$; X is O or S(O)$_n$; n is 0 or an integer of from 1 to 2;

$R_3$ is selected from the group consisting of H, hydroxyl, $C_{1-5}$ alkyl, $C_{1-5}$ alkylOR$_{13}$, and $C_{1-5}$ alkylN(R$_{13}$)$_2$;

$R_4$ is selected from the group consisting of H, $C_{2-5}$ alkenyl, $C_{1-5}$ alkyl, $C_{1-5}$ alkylOR$_{13}$ and $C_{1-5}$ alkylN(R$_{13}$)$_2$;

$R_5$, $R_6$, $R_7$, $R_8$, $R_9$, $R_{10}$, $R_{11}$, and $R_{12}$ are independently selected from the group consisting of H, $C_{1-5}$ alkyl, $C_{1-5}$ alkyl $OR_{13}$ and $OR_{13}$, or $R_5$ may represent O; and $R_{13}$ is selected from the group consisting of H, $C_{1-5}$ alkyl and $C_{3-8}$ cyclic alkyl.

2. The compound of claim 1 wherein R is selected from the group consisting of hydrogen, methyl, bromo and chloro; $R_1$ is selected from the group consisting of hydrogen and chloro, $R_2$ is hydrogen, $R_3$ is methyl, $R_5$, $R_6$, $R_7$, $R_9$, $R_{10}$, and $R_{11}$ are hydrogen and $R_4$ is isopropenyl.

3. The compound of claim 2 wherein said compound is 4-(1-isopropyl-4-methyl-1,2,5,6-tetra-hydropyridin-2-yl)-5-methylbenzene-1,3-diol.

4. A composition which is an ophthalmic solution comprising a therapeutically effective amount of a compound according to claim 1 and an ophthalmically acceptable pharmaceutical excipient.

5. The composition of claim 4, wherein the ophthalmic solution further comprises at least one ingredient selected from the group of an ophthalmically acceptable preservative, buffer system, antioxidant and chelating agent.

6. A composition comprising a container adapted to dispense its contents in metered form and a composition which is an ophthalmic solution as defined in claim 4.

7. The composition of claim 4, wherein said compound is 4-(1-isopropyl-4-methyl-1,2,5,6-tetra-hydropyridin-2-yl)-5-methylbenzene-1,3-diol.

* * * * *

UNITED STATES PATENT AND TRADEMARK OFFICE
CERTIFICATE OF CORRECTION

PATENT NO. : 7,618,966 B2
APPLICATION NO. : 11/409871
DATED : November 17, 2009
INVENTOR(S) : June Chen et al.

It is certified that error appears in the above-identified patent and that said Letters Patent is hereby corrected as shown below:

In column 1, line 31-32, delete "pupilary" and insert -- pupillary --, therefor.

In column 3, line 55-60, after " 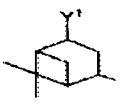 " delete ".".

In column 7, line 47, after "8462" insert -- . --.

In column 11, line 6, delete "chlolinesterase" and insert -- cholinesterase --, therefor.

In column 11, line 11, delete "dextrophan, detromethorphan," and insert -- dextrorphan, dextromethorphan, --, therefor.

In column 11, line 23, delete "chloprostenol," and insert -- cloprostenol, --, therefor.

In column 11, line 24, delete "chloprostenol," and insert -- cloprostenol, --, therefor.

In column 11, line 34-35, delete "pneumatonometry" and insert -- pneumatonometer --, therefor.

In column 12, line 45, after "solution" insert -- was --.

In column 15, line 63, after "(10.3 g)" insert -- . --.

In column 17, line 67, delete "??1.7" and insert -- δ 1.7 --, therefor.

In column 18, line 1, delete "2.7)" and insert -- 2,7) --, therefor.

In column 18, line 6, delete "dihydropyidine" and insert -- dihydropyridine --, therefor.

In column 18, line 7, delete "?" and insert -- δ --, therefor.

In column 18, line 29, delete "δ?1.55" and insert -- δ 1.55 --, therefor.

In column 18, line 33-34, delete "dihydropyidine" and insert -- dihydropyridine --, therefor.

In column 18, line 38, delete "3.8)," and insert -- 3,8), --, therefor.

In column 18, line 59, delete "??1.67" and insert -- δ 1.67 --, therefor.

In column 18, line 62, delete "2.8)," and insert -- 2,8), --, therefor.

In column 19, line 5, delete "3.8)," and insert -- 3,8), --, therefor.

In column 19, line 14, after "(m, 2H)" insert -- . --.

In column 19, line 26, delete "δ?1.6" and insert -- δ 1.6 --, therefor.

In column 20, line 5, delete "wahed" and insert -- washed --, therefor.

In column 20, line 20, after "was" insert -- : --.

Signed and Sealed this

Thirtieth Day of March, 2010

David J. Kappos
*Director of the United States Patent and Trademark Office*